(12) United States Patent
Fahnestock et al.

(10) Patent No.: US 7,060,260 B2
(45) Date of Patent: Jun. 13, 2006

(54) WATER-SOLUBLE SILK PROTEINS IN COMPOSITIONS FOR SKIN CARE, HAIR CARE OR HAIR COLORING

(75) Inventors: Stephen R. Fahnestock, Wilmington, DE (US); Thomas M. Schultz, Randolph, NJ (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 10/772,124

(22) Filed: Feb. 4, 2004

(65) Prior Publication Data

US 2004/0170590 A1  Sep. 2, 2004

Related U.S. Application Data

(60) Provisional application No. 60/448,952, filed on Feb. 20, 2003.

(51) Int. Cl.
*A61K 8/64* (2006.01)
*A61K 8/02* (2006.01)

(52) U.S. Cl. .................. 424/78.03; 424/401; 514/12; 514/350

(58) Field of Classification Search ............. 424/401; 514/12, 350
See application file for complete search history.

(56) References Cited

U.S. PATENT DOCUMENTS

| | | | |
|---|---|---|---|
| 4,416,873 A * | 11/1983 | Puchalski et al. .............. 514/8 |
| 4,482,537 A * | 11/1984 | El-Menshawy et al. ........ 424/59 |
| 5,490,980 A * | 2/1996 | Richardson et al. ........ 424/94.6 |
| 5,504,228 A * | 4/1996 | Morelle et al. ............... 554/69 |
| 5,728,810 A * | 3/1998 | Lewis et al. ................ 530/353 |
| 5,733,771 A * | 3/1998 | Lewis et al. ............. 435/252.3 |
| 5,747,015 A * | 5/1998 | Oshika et al. ........... 424/70.14 |
| 5,756,677 A * | 5/1998 | Lewis et al. ................ 530/353 |
| 5,760,004 A * | 6/1998 | Stedronsky .................. 514/21 |
| 5,989,894 A * | 11/1999 | Lewis et al. ............. 435/252.3 |
| 5,994,099 A * | 11/1999 | Lewis et al. ............... 435/69.1 |
| 6,013,250 A * | 1/2000 | Cannell et al. ........... 424/70.51 |
| 6,139,851 A * | 10/2000 | Omura et al. ................ 424/401 |
| 6,268,169 B1 * | 7/2001 | Fahnestock ................ 435/69.1 |
| 6,280,747 B1 * | 8/2001 | Philippe et al. ............. 424/401 |
| 2002/0064539 A1 * | 5/2002 | Philippe et al. ............. 424/401 |
| 2004/0132978 A1 * | 7/2004 | Fahnestock et al. ......... 530/353 |

FOREIGN PATENT DOCUMENTS

| | | |
|---|---|---|
| DE | 3139438 A1 | 4/1983 |
| DE | 10113781 A1 | 12/2001 |
| EP | 0230702 A1 | 8/1987 |
| JP | 63092671 | 4/1988 |
| JP | 02311412 | 12/1989 |
| JP | 07067687 | 3/1995 |
| JP | 08027186 | 1/1996 |
| JP | 2574732 B2 | 1/1997 |
| JP | 309816 | 12/1997 |
| WO | WO 01/90389 A2 * | 11/2001 |
| WO | WO 03/020916 A2 | 3/2003 |

OTHER PUBLICATIONS

U.S. Appl. No. 10/704,337, filed Nov. 7, 2003, Fahnestock et al.
Winkler et al.,Designing recombinant spider silk proteins to control assembly, Int. J. Biol. Macromol. vol. 24: pp. 265-270, 1999.
Arcidiacono et al., Purification and characterization of recombinant spider silk expressed in *Escherichia coli,* Appl. Microbiol. Biotechnol. vol. 49: pp. 31-38.
Foelix, R. F., Spider Webs, Biology of Spiders, pp. 109-121, Harvard University Press Cambridge, MA 1992.
Ohshima et al., Cloning of the silk fibroin gene and its flanking sequences, Proc. Natl. Acad. Sci. USA, vol. 74: pp. 5363-5367, 1977.
Xu et al., Structure of a protein superfiber: Spider dragline silk, Proc. Natl. Acad. Sci. U.S.A., vol. 87: pp. 7120-7124, 1990.
Hinman et al., Isolation of a Clone Encoding a Second Dragline Silk Fibroin, J. Biol. Chem., vol. 267: pp. 19320-19324, 1992.
Arcidiacono et al., Aqueous Processing and Fiber Spinning of Recombinant Spider Silks, Macromolecules, vol. 35:pp. 1262-1266, 2002.
Fahnestock, Microbial Production of Spider Silk Proteins, Rev. Mol. Biotechnol. 74: pp. 105-119, 2000.
Lazaris et al., Spider Silk Fibers Spun from Soluble Recombinant Silk Produced in Mamalian Cells, Science vol. 295: pp. 472-476, 2002.

* cited by examiner

Primary Examiner—Robert A. Wax

(57) ABSTRACT

Skin care, hair care and hair coloring compositions comprising a water-soluble silk protein as an active ingredient are described. The water-soluble silk protein deposits onto the skin or the natural hair keratin to provide a smooth and durable film to provide added strength for protection against environmental, chemical, and grooming associated damage. The compositions may be in the form of skin care, skin cleansing, or anti-wrinkle products, shampoos, conditioners, lotions, aerosols, gels, mousses, dyes, or bleaches.

20 Claims, No Drawings

WATER-SOLUBLE SILK PROTEINS IN COMPOSITIONS FOR SKIN CARE, HAIR CARE OR HAIR COLORING

This invention claims the benefit of U.S. Provisional Application No. 60/448,952 filed in the USPTO on Feb. 20, 2003.

FIELD OF THE INVENTION

The invention relates to the field of personal care products. More specifically, the invention relates to the use of water-soluble silk proteins in compositions for skin care, hair care or hair coloring products.

BACKGROUND OF THE INVENTION

Film-forming substances are widely used in compositions for skin care and hair care as conditioning agents and moisturizers, and to protect the skin and hair against environmental and chemical damage. These substances adsorb onto and/or absorb into the skin or hair, forming a protective coating. Commonly used film-forming substances include synthetic polymers, such as silicones, polyvinylpyrrolidone, acrylic acid polymers, and polysaccharides, and proteins, such as collagen, keratin, elastin, and silk proteins. Proteins are known to be particularly effective film-forming agents. Because of their low solubility at the conditions used in skin and hair care products, proteins are commonly used in the form of peptides, formed by the hydrolysis of the protein.

In hair care compositions, film-forming substances are used to form a protective film on the surface of the hair to protect it from damage due to grooming and styling, shampooing, and exposure to ultraviolet light and the reactive chemicals commonly used in permanent wave agents, hair coloring products, bleaches, and hair straighteners, which denature the hair keratin protein. Moreover, these film-forming substances improve the elasticity of the hair. Film-forming substances that have been used in hair care products include proteins, such as keratin and collagen and hydrolysates thereof, and polymeric materials, such as polyacrylates, long chain alkyl quaternized amines, and siloxane polymers. For example, Cannell at al. in U.S. Pat. No. 6,013,250 describe a hair care composition for treating hair against chemical and ultraviolet light damage. This composition comprises hydrolyzed protein, having an abundance of sulfur containing amino acids, and divalent cations. Omura et al. in U.S. Pat. No. 6,139,851 describe a hair care cosmetic for treating split ends which contains one or more types of silicone derivatives, one or more types of specific polyether modified silicone, and a lower alcohol. The major problem with these compositions is that they lack the required durability required for long-lasting protection.

Film-forming substances are also used in skin care compositions to form a protective film on the skin. This film lubricates and coats the skin to passively impede the evaporation of moisture and smoothes and softens the skin. Commonly used film-forming substances in skin care compositions include hydrolyzed animal and vegetable proteins (Puchalski et al., U.S. Pat. No. 4,416,873, El-Menshawy et al., U.S. Pat. No. 4,482,537, and Kojima et al., JP 02311412).

Silk proteins have also been used as film-forming substances in skin care and hair care compositions. Because of the low solubility of these proteins, they are used in the form of protein hydrolysates. Silk proteins are ideally suited for film-forming and coating applications because of their ability to self-assemble in solution (Winkler et al., *Int. J. Biol. Macromol.* 24:265–270 (1999)). This self-assembly property of silk proteins is due to the formation of anti-parallel beta-pleated sheets via hydrogen bonding and hydrophobic interactions (Arcidiacono et al., *Appl. Microbiol. Biotechnol.* 49:31–38 (1998)). Silk proteins are produced by over 30,000 species of spiders and by many insects particularly in the order *Lepidoptera* (Foelix, R. F. *Biology of Spiders*, Harvard University Press Cambridge, Mass. (1992)). Few of these silk proteins have been studied in detail. The cocoon silk of the domesticated silkworm *Bombyx mori*, i.e. silk fibroin, and the dragline silk of the orb-weaving spider *Nephila clavipes* are among the best characterized.

Recombinant DNA technology has been used to provide a more practical source of silk proteins. Ohshima et al. (*Proc. Natl. Acad. Sci. USA*, 74:5363–5367 (1977)) report the cloning of the silk fibroin gene complete with flanking sequences of the silkworm *Bombyx mori* into *E. coli* Petty-Saphon et al. (EP 0230702) disclose the recombinant production of silk fibroin and silk sericin from a variety of hosts including *E. coli, Sacchromyces cerevisiae, Pseudomonas sp., Rhodopseudomonas sp., Bacillus sp.,* and *Strepomyces sp.* The production of recombinant spider silk proteins is also known. Xu et al. (*Proc. Natl. Acad. Sci. U.S.A.*, 87:7120–7124 (1990)) report the determination of the sequence for a portion of the repetitive sequence of a dragline spider silk protein, Spidroin 1, from the spider *Nephila clavipes,* based on a partial cDNA clone. Hinman and Lewis (*J. Biol. Chem.* 267:19320–19324 (1992)) report the sequence of a partial cDNA clone encoding a portion of the repeating sequence of a second fibroin protein, Spidroin 2, from dragline silk of *Nephila clavipes.* Lewis et al. (U.S. Pat. Nos. 5,728,810 and 5,989,894) disclose the expression of spider silk proteins including protein fragments and variants of *Nephila clavipes* from transformed *E. coli.* cDNA clones encoding minor ampullate spider silk proteins and the expression thereof is described by Lewis et al. (U.S. Pat. Nos. 5,733,771 and 5,756,677). Lewis et al. (U.S. Pat. No. 5,994,099) describe the cloning of cDNA encoding the flagelliform silk protein from an orb-web spinning spider. Fahnestock (U.S. Pat. No. 6,268,169) describes novel spider silk analog proteins derived from the amino acid consensus sequence of repeating units found in the natural spider dragline of *Nephila clavipes.* The synthetic spider dragline was produced from *E. coli, Bacillus subtilis,* and *Pichia pastoris* recombinant expression systems. Lewis et al. (WO 03/020916) describe the cloning of spider silk proteins from the major ampullate glands of *Nephila madagascariensis, Nephila senegalensis, Tetragnatha kauaiensis, Tetragnatha versicolor, Argiope aurantia, Argiope trifasciata, Gasteracantha mammosa,* and *Latrodectus geometricus,* the flagelliform glands of *Argiope trifasciata,* the ampullate glands of *Dolomedes tenebrosus,* two sets of silk glands from *Plectreurys tristis,* and the silk glands of the mygalomorph *Euagrus chisoseus.*

The solubility of recombinant silk proteins in aqueous solution depends on the type of silk protein as well as the expression system used. Recombinant silkworm silk proteins are expressed in insoluble form and can only be dissolved using harsh solvents. Recombinant spider silk proteins are expressed in soluble form in bacterial hosts and in both soluble and insoluble forms in yeasts. However, the recombinant spider silk proteins that are expressed in soluble form in microbial systems become insoluble upon purification and are extremely difficult to resolubilize after drying or precipitation (Arcidiacono et al., *Macromolecules* 35:1262–1266 (2002)), limiting applications which require processing of the proteins into different types of fibers, films or coatings. Winkler et al. (*Int. J. Biol. Macromol.* 24:265–270 (1999)) report that recombinant spider silk proteins rapidly self-assemble upon purification to form insoluble microfibrils. Fahnestock (*Rev. Mol. Biotechnol.* 74:105–119 (2000)) also reports that once spider silk analog proteins were precipitated, they could only be redissolved in denaturing solvents, such as aqueous quanidine hydrochloride or hexafluoroisopropanol. However, a purification method which results in a silk protein or analog protein that can be redissolved in water after precipitation is described by Fahnestock et al. (copending, co-owned U.S. patent application Ser. No. 10/704,337, filed Nov. 7, 2003, entitled "A Method for Purifying and Recovering Silk Proteins in Soluble Form and Uses Thereof"). In that method, the silk protein is precipitated from the cell extract by the addition of a salt, such as ammonium sulfate, at a temperature below 20° C. The recovered protein is readily redissolved in water.

The water solubility of spider silk proteins expressed in plants is reported to be much higher than that of the microbially expressed proteins, as they are readily soluble in aqueous buffers (Scheller et al. DE 10113781). Additionally, Lazaris et al. (*Science* 295:472–476 (2002)) describe the production of soluble recombinant spider silk protein produced in mammalian cells. After precipitation, this spider silk protein was readily redissolved in phosphate-buffered saline. The solubility of the spider silk proteins produced in mammalian cells was attributed to the presence of the COOH-terminus in these proteins, which makes them more hydrophilic. These COOH-terminal amino acids are absent in spider silk proteins expressed in microbial hosts.

There has been no description in the art of the use of soluble, intact silk proteins in skin care, hair care, or hair coloring compositions. Silk proteins from the silkworm *Bombyx mori* have been used in cosmetic compositions including hair care products. However, these silk proteins are only soluble in harsh solvents that are not compatible with skin care and hair care products. Consequently, these silk proteins have been used in the form of silk protein peptides, formed by the hydrolysis of the silk protein (Kuroda et al., JP 309816; Terada et al., JP 08027186; Otoi et al., JP 63092671; Inoe et al., JP 2574732; and Yamaguchi et al., JP 07067687). Morelle et al. in U.S. Pat. No. 5,504,228 describe the use of acylated silk fibroin hydrolysates in cosmetics. Additionally, Oshika et al. in U.S. Pat. No. 5,747,015 describe a hair care product which comprises a salt of an acylated compound obtained by condensing fatty acids with silk protein-derived peptides, which were obtained by the hydrolysis of silk protein. While providing some beneficial coating effect, the silk protein peptides are not as effective as film-forming agents as the soluble, intact proteins. Ritter et al. (DE 3139438) describe the use of colloidal silk protein as an additive in hair care products. However, the colloidal silk protein is not as effective in film forming and coating for skin or hair treatment as a soluble, intact silk protein.

Philippe et al. in U.S. Pat. No. 6,280,747 describe the use of natural or recombinant spider silk proteins in cosmetic and dermatological compositions such as hair care, skin care, make-up, and sunscreen products. However, the spider silk proteins described in that disclosure are not water-soluble. Therefore, the beneficial effects of the self-assembly and coating properties of the spider silk proteins are not fully realized.

In view of the above, there is a need for a novel class of hair care and hair coloring compositions that provide superior durability and long-lasting protection from the various activities mentioned above that cause hair damage. Additionally, there is a need for a novel class of skin care compositions that provide a superior smooth and durable, protective coating as well as added strength to the skin.

SUMMARY OF THE INVENTION

The invention provides for a skin care, hair care or hair coloring composition comprising:
(a) an effective amount of a water-soluble silk protein; and optionally
(b) at least one cosmetic adjuvant selected from the group consisting of fillers, surfactants, thixotropic agents, antioxidants, preserving agents, dyes, pigments, fragrances, thickeners, vitamins, hormones, moisturizers, UV absorbing sunscreens, wetting agents, cationic polymers, anionic polymers, nonionic polymers, amphoteric polymers, and hair coloring active substances.

The effective amount of the water-soluble silk protein is preferably from about 0.001 to about 90% by weight of the total weight of the composition, about 0.001 to about 60% by weight of the total weight of the composition, or about 0.01 to about 20% by weight of the total weight of the composition.

The water-soluble silk protein can be in a derivatized form. If so, the water-soluble silk protein is preferably derivatized with a functional group selected from the group consisting of amines, oxanes, cyanates, carboxylic acid esters, silicone copolyols, siloxane esters, quaternized amine aliphatics, urethanes, polyacrylamides, dicarboxylic acid esters, and halogenated esters.

The water-soluble silk protein preferably is selected from the group consisting of the dragline spider silk proteins Spidroin 1 and Spidroin 2, spider silk proteins originating from the minor ampullate gland of *Nephila clavipes,* and spider silk proteins originating from the flagelliform gland of *Nephila clavipes,* and variants thereof. More preferably, the spider silk dragline protein is defined by the formula:

[AGQGGYGGLGXQGAGRGGLGGQGAGA$_n$GG]$_z$, 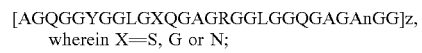
wherein X=S, G or N;

n=0–7 and z=1–75, and wherein the value of z determines the number of repeats in the variant protein and wherein the formula encompasses variations selected from the group consisting of:
(a) when n=0, the sequence encompassing AGRGGLG-GQGAGA$_n$GG is deleted;
(b) deletions other than the poly-alanine sequence, limited by the value of n will encompass integral multiples of three consecutive residues;
(c) the deletion of GYG in any repeat is accompanied by deletion of GRG in the same repeat; and
(d) where a first repeat where n=0 is deleted, the first repeat is preceded by a second repeat where n=6; and wherein the full-length protein is encoded by a gene or genes and wherein said gene or genes are not endogenous to the *Nephila clavipes* genome.

Even more preferably, the spider dragline protein has a repeating unit having the amino acid sequence as set forth in SEQ ID NO:1, SEQ ID NO:2, or SEQ ID NO:3.

Alternatively, the spider silk dragline protein is more preferably defined by the formula:

[GPGGYGPGQQGPGGYGPGQQGPGGYG-
PGQQGPSGPGSA$_n$]$_z$, 

wherein n=6–10 and z=1–75 and wherein, excluding the poly-alanine sequence, individual repeats differ from the consensus repeat sequence by deletions of integral multiples of five consecutive residues consisting of one or both of the pentapeptide sequences GPGGY or GPGQQ and wherein the full-length protein is encoded by a gene or genes and wherein the gene or genes are not endogenous to the *Nephila clavipes* genome. Even more preferably, the spider dragline protein has a repeating unit having the amino acid sequence as set forth in SEQ ID NO:4.

The skin care, hair care, or hair coloring composition described above can further comprise an effective amount of a natural or recombinant protein, or a digest thereof. The effective amount of the natural or recombinant protein preferably is from about 0.001 to about 60% by weight of the total weight of the composition or about 0.01 to about 20% by weight of the total weight of the composition. The natural or recombinant protein preferably is selected from the group consisting of wheat proteins, oat proteins, rice proteins, almond proteins, soy proteins, collagen, keratins, gelatin, elastin, fibronectin, and soluble reticulin.

The skin care, hair care, or hair coloring composition described above can be an anhydrous composition containing a fatty phase, the fatty phase containing at least one liquid, solid, or semi-solid fatty substance, or in the form of an aqueous solution containing mono or polyhydric alcohols. If the composition is an anhydrous composition, the fatty substance preferably is selected from the group consisting of isododecane, hydrogenated polyisobutene, squalane, isononyl isononanoate, cyclotetra-and-pentadimethicones, phenyltrimethicone, ethylene homopolymers, ethoxylated fats and oils, fluoroalkanes, microcrystalline waxes, ozocerite, beeswax, seracite, shea butter, candelilla wax, arachidyl propionate, fluoropolymers represented by the monomer $CH_2$—CH—$F_y$, wherein x=1 or 2, and y=1, 2 or 3, and copolymers of ethylene and of at least one monomer represented by the formula $CH_2$=CH—$R_3$, wherein $R_3$ is an alkyl radical containing from 1 to 30 carbon atoms or an aryl or aralkyl radical.

Alternatively, the skin care, hair care, or hair coloring composition described above can be in the form of a creme emulsion, a gel, a dry powder, an aerosol, a mousse, an alcohol-in-oil emulsion, an alcohol and water solution, an aqueous solution, or an emulsion solution. Preferably, these compositions further comprise a carbomer, gum, or other thickener in a proportion of from about 0.1 to about 15% by weight relative to the total weight of the composition. Alternatively, at least one of the materials found in the composition is in the form of a powder and the effective amount of the water-soluble silk protein is present along with a pigment or filler. More preferably, the effective amount of the water-soluble silk protein is from about 0.001 to about 60% by weight of the total weight of the composition. The water-soluble silk protein can be in a derivatized form as described above.

Additionally, the skin care, hair care, or hair coloring composition described above can be in the form of an aqueous alkaline solution suitable for preparing compositions for coloring or bleaching hair. Preferably, the skin care, hair care, or hair coloring composition described above further comprises a direct hair dye, an oxidative hair dye, or a peroxygen-based oxidizing agent for bleaching hair.

The skin care, hair care, or hair coloring composition described above can also be in the form of a stable dispersion of water-in-oil or oil-in-water type.

Additionally, the invention provides a method for forming a protective film of water-soluble silk protein on skin or hair comprising:

(a) applying to the skin or hair the skin care, hair care, or hair coloring composition described above; and
(b) allowing the formation of the water-soluble silk protein protective film on the skin or hair.

The invention also provides a method for coloring or bleaching hair comprising applying the aqueous alkaline solution described above to the hair for a period of time sufficient to cause the coloration of the hair. Preferably, the aqueous alkaline solution is applied to the hair for a period of about 5 to about 50 minutes.

BRIEF DESCRIPTION OF THE FIGURES AND SEQUENCE DESCRIPTIONS

The invention can be more fully understood from the following detailed description and the accompanying sequence descriptions, which form a part of this application.

The following sequences conform with 37 C.F.R. 1.821–1.825 ("Requirements for Patent Applications Containing Nucleotide Sequences and/or Amino Acid Sequence Disclosures—the Sequence Rules") and are consistent with World Intellectual Property Organization (WIPO) Standard ST. 25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

SEQ ID NO:1 is the amino acid sequence of the monomer of the spider silk DP-1A analog protein.

SEQ ID NO:2 is the amino acid sequence of the monomer of the spider silk DP-1B.9 analog protein.

SEQ ID NO:3 is the amino acid sequence of the monomer of the spider silk DP-1B.16 analog protein.

SEQ ID NO:4 is the amino acid sequence of the monomer of the spider silk DP-2A analog protein.

SEQ ID NO:5 is the amino acid sequence of the consensus repeat sequence representing spider silk analog protein DP-1.

SEQ ID NO:6 is the amino acid sequence of a portion of the consensus repeat sequence representing spider silk analog protein DP-1.

SEQ ID NO:7 is the amino acid sequence of one of the repeat sequences representing the spider silk analog protein DP-1.

SEQ ID NO:8 is the amino acid sequence of one of the repeat sequences representing the spider silk analog protein DP-1.

SEQ ID NO:9 is the amino acid sequence of the consensus repeat sequence representing spider silk analog protein DP-2.

SEQ ID NOs:10 and 11 are the amino acid sequences of possible deletions in the consensus repeat sequence representing snider silk analog protein DP-2.

SEQ ID NOs: 12–14 are the amino acid sequence of three of the repeat sequences representing the spider silk analog protein DP-2.

DETAILED DESCRIPTION OF THE INVENTION

Applicants have solved the stated problem by unexpectedly discovering that water-soluble silk proteins form deposits onto and into natural hair keratin to give it a smooth and durable protective coating and added strength and durability, as seen by a dramatic increase in resistance to combing and stress damage. Moreover, the natural protective and ultra-violet light barrier properties of the silk protein reduce significantly the hair color loss from exposure to sunlight. Additionally, applicants have discovered that water-soluble silk proteins form deposits onto the skin to give it a smooth and durable, protective coating as well as added strength as seen by a dramatic increase in resistance to trans-epidermal water loss and an increase in torsional properties. Moreover, the natural protective and UV barrier function of the silk protein serves to protect against erythema.

The following definitions are used herein and should be referred to for interpretation of the claims and the specification.

"Nucleic acid" refers to a molecule which can be single stranded or double stranded, composed of monomers (nucleotides) containing a sugar, phosphate and either a purine or pyrimidine. In bacteria, lower eukaryotes, and in higher animals and plants, "deoxyribonucleic acid" (DNA) refers to the genetic material while "ribonucleic acid" (RNA) is involved in the translation of the information from DNA into proteins.

The terms "polypeptide" and "protein" are used interchangeably.

The term "peptide" is used to describe a subunit of a polypeptide or protein formed by hydrolysis.

The terms "hydrolysis" and "digestion" are used interchangeably herein to refer to processes by which proteins are cleaved into smaller peptide units. The resulting peptide mixture is referred to as a "hydrolysate" or "digest".

The term "natural protein" is used to describe a protein that is isolated from its native animal or plant source.

The term "recombinant protein" is used to describe a protein that is produced by a non-native organism using genetic engineering techniques. Both natural proteins and recombinant proteins can exist in their native sequences or in sequences modified by genetic engineering.

"Gene" refers to a nucleic acid fragment that expresses a specific protein, including regulatory sequences preceding (5' non-coding sequences) and following (3' non-coding sequences) the coding sequence.

"Codon" refers to a unit of three nucleotides that encodes a single amino acid.

As used herein, "transformation" is the acquisition of new genes in a cell by the incorporation of nucleic acid.

The term "expression" as used herein is intended to mean the transcription and translation to gene product from a gene coding for the sequence of the gene product. In the expression, a DNA chain coding for the sequence of gene product is first transcribed to a complementary RNA which is often a messenger RNA and, then, the thus transcribed messenger RNA is translated into the above-mentioned gene product if the gene product is a protein.

The terms "silk variant protein" and "silk analog protein" are used interchangeably herein to refer to a designed protein, the amino acid sequence of which is based on repetitive sequence motifs and variations thereof that are found in known natural silk proteins.

The term "full length variant protein" will refer to any silk variant protein encoded by a synthetic gene which has been constructed by the assembly and polymerization of a DNA monomer.

The term "DNA monomer" will refer to a DNA fragment consisting of between 300 and 400 bp which encodes one or more repeating amino acid sequences of a silk variant protein.

The term "peptide monomer" or "polypeptide monomer" will refer to the amino acid sequence encoded by a DNA monomer.

The term "DP-1 analog" will refer to any spider silk variant protein derived from the amino acid sequence of the natural Protein 1 (Spidroin 1) of *Nephila calvipes*.

The term "DP-2 analog" will refer to any spider silk variant protein derived from the amino acid sequence of the natural Protein 2 (Spidroin 2) of *Nephila calvipes*.

As used herein the following abbreviations will be used to identify specific amino acids:

| Amino Acid | Three-Letter Abbreviation | One-Letter Abbreviation |
| --- | --- | --- |
| Alanine | Ala | A |
| Arginine | Arg | R |
| Asparagine | Asn | N |
| Aspartic acid | Asp | D |
| Asparagine or aspartic acid | Asx | B |
| Cysteine | Cys | C |
| Glutamine | Gln | Q |
| Glutamine acid | Glu | E |
| Glutamine or glutamic acid | Glx | Z |
| Glycine | Gly | G |
| Histidine | His | H |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

The present invention comprises skin care, hair care, or hair coloring compositions comprising an effective amount of a water-soluble silk protein in a suitable cosmetic carrier. The compositions according to the present invention include, but are not limited to, skin care, skin cleansing, make-up, and anti-wrinkle products, and shampoos, hair conditioners, hair treatment creams, styling gels, mousses, hair sprays, set lotions, blow-styling lotions, hair color lotions, hair relaxing compositions, permanent wave first agents and permanent wave second agents.

A water-soluble silk protein is herein defined as a silk protein or analog, having a glycine-rich sequence, herein referred to as the soft segment, alternating with an oligomer of polyalanine, herein referred to as the hard segment, in which at least about 20% of the soft segment is composed of glycine and about 70–100% of the hard segment is composed of alanine. The length of the hard segment is between about 5 to 100 amino acids, while the length of the soft segment is between about 5 to 300 amino acids. These soluble silk proteins redissolve in aqueous solution after precipitation without the addition of harsh chemicals such as acids or denaturants. These silk proteins are further characterized by forming anti-parallel beta-pleated sheets in solution via hydrogen bonding and hydrophobic interactions, resulting in self-assembly. This property renders these proteins ideal for use in film-forming and coating applications, such as skin care and hair care. Additionally, insoluble natural or recombinant silk proteins may be chemically modified to make them water-soluble by reaction with a polar, low molecular weight reactant, as described by Stedronsky in U.S. Pat. No. 5,760,004, incorporated herein by reference. For example, the silk protein may be modified to incorporate hydroxyl, sulfonato, or ammonio groups, which increase the solubility of the protein.

Recombinant proteins typically have specific and narrowly defined molecular weights from about five thousand to several hundred thousand daltons, depending on the nature of the protein. While recombinant silk proteins of low molecular weight favor absorption, they are more easily lost from the skin or hair by subsequent washing. On the other hand, silk proteins of very high molecular weight do not penetrate well. Generally, an average molecular weight of 500,000 daltons or less is desirable for the silk proteins utilized in this invention. The preferred water-soluble silk proteins of this invention have an average molecular weight of from about 40,000 to about 500,000 daltons, more preferably from about 60,000 to about 100,000 daltons.

The silk proteins include, but are not limited to, spider silk proteins and spider silk analog proteins. Analog silk proteins are herein defined as polypeptides that imitate the repeating units of amino acids of natural silk proteins. The terms "analog silk protein" and "silk variant protein" are herein used interchangeably. For example, the silk protein may be recombinant dragline spider silk protein, specifically, Spidroin 1 or Spidroin 2, or variants thereof, originating from the major ampullate gland of *Nephila clavipes,* as described by Lewis et al. in U.S. Pat. Nos. 5,728,810 and 5,989,894, incorporated herein by reference. Additionally, the silk protein may be the recombinant spider silk proteins originating from the minor ampullate gland of *Nephila clavipes,* or variants thereof, as described by Lewis in U.S. Pat. Nos. 5,733,771 and 5,756,677, incorporated herein by reference. The silk protein may also be the recombinant silk protein originating from the flagelliform gland of *Nephila clavipes,* or variants thereof, as described by Lewis in U.S. Pat. No. 5,994,099, incorporated herein by reference. The silk protein may also be one or more of those described by Lewis et al. in *Protein Expression and Purification* 7:400–406 (1996), or by Prince et al., in *Biochemistry* 34:10879–10885 (1995), or by Winkler et al. in *Int. J. Biol. Macromol.* 24:265–270 (1999). The silk protein may also be the recombinant silk protein originating from the major ampullate glands of *Nephila madagascariensis, Nephila senegalensis, Tetragnatha kauaiensis, Tetragnatha versicolor, Argiope aurantia, Argiope trifasciata, Gasteracantha mammosa,* and *Latrodectus geometricus,* the flagelliform glands of *Argiope trifasciata,* the ampullate glands of *Dolomedes tenebrosus,* the silk glands from *Plectreurys tristis,* and the silk glands of the mygalomorph *Euagrus chisoseus* as described by Lewis et al. in WO 03/020916, incorporated herein by reference.

Moreover, the silk protein may be a variant designed to possess certain beneficial properties. For example, the silk protein variant may be designed to have increased elasticity by elongating the glycine-rich (soft) segment, as described in patent applications WO 9116351 and EP 452925, both of which are incorporated herein by reference. Conversely, it is possible to reduce the elasticity of the silk protein by shortening the glycine-rich segment. Similarly, replacement of the glycine residues with serine residues results in a less rigid silk protein.

The preferred water-soluble silk proteins of the present invention are spider silk analog proteins, as described by Fahnestock in U.S. Pat. No. 6,268,169, incorporated herein by reference. These silk proteins are analog proteins of the natural dragline spider silk Spidroin 1 (DP-1) and Spidroin 2 (DP-2) proteins of *Nephila calvipes.* Two analogs of DP-1 were designed and designated DP-1A and DP-1B. DP-1A is composed of a tandemly repeated 101-amino acid sequence. The 101-amino acid "peptide monomer", given as SEQ ID NO:1, comprises four repeats which have different patterns that reflect the variation of the individual repeating units of DP-1 from the consensus sequence. This 101-amino acid long peptide monomer (SEQ ID NO:1) was repeated from 1 to 16 times in a series of analog proteins. DP-1B was designed by reordering the four repeats within the monomer of DP-1A. Two sets of genes using different codons were designed to produce DP-1B, specifically DP-1B.9 and DP-1B.16. The resulting amino acid monomer sequences are given as SEQ ID NO:2 for DP-1B.9 and SEQ ID NO:3 for DP-IB.16. The sequence of DP-1 B matches the natural sequence of Spidroin I more closely over a more extended segment than does DP-1A. The DP-1 amino acid sequences and similar analogs may be represented by the following consensus repeat formula (SEQ ID NO:5):

[AGQGGYGGLGXQGAGRGGLGGQGAGAnGG]z       (1)

wherein X=S, G or N; n=0–7 and z=1–75, and wherein the value of z determines the number of repeats in the variant protein. The formula encompasses variations selected from the group consisting of: (a) when n=0, the sequence encompassing AGRGGLGGQGAGAnGG, given as SEQ ID NO:6, is deleted, resulting in the sequence given as SEQ ID NO:7; (b) deletions other than the poly-alanine sequence, limited by the value of n will encompass integral multiples of three consecutive residues; (c) the deletion of GYG in any repeat is accompanied by deletion of GRG in the same repeat, resulting in the sequence given as SEQ ID NO:8; and (d) where a first repeat where n=0 is deleted, the first repeat is preceded by a second repeat where n=6; and wherein the full-length protein is encoded by a gene or genes and wherein said gene or genes are not endogenous to the *Nephila clavipes* genome.

Synthetic analogs of DP-2 were designed to mimic both the repeating consensus sequence of the natural protein and the pattern of variation among individual repeats of Spidroin 2. The analog DP-2A, given as SEQ ID NO:4, is composed of a tandemly repeated 119-amino acid sequence. This 119-amino acid "peptide monomer" comprises three repeats which have different patterns. This 119-amino acid long peptide monomer was repeated from 1 to 16 times in a series of analog proteins. The spider silk analog protein DP-2A is the most preferred water-soluble silk protein of the present invention. The DP-2 amino acid sequence and similar analogs may be represented by the following consensus repeat formula (SEQ ID NO:9):

[GPGGYGPGQQGPGGYGPGQQGPGGYG-
PGQQGPSGPGSAn]z       (2)

wherein n=6–10 and z=1–75 and wherein, excluding the poly-alanine sequence, individual repeats differ from the consensus repeat sequence by deletions of integral multiples of five consecutive residues consisting of one or both of the pentapeptide sequences GPGGY (SEQ ID NO:10) or GPGQQ (SEQ ID NO:11), resulting in the sequences given as SEQ ID NOs:12–14, and wherein the full-length protein is encoded by a gene or genes and wherein the gene or genes are not endogenous to the *Nephila clavipes* genome.

The water-soluble silk proteins may be prepared by transformed prokaryotic or eukaryotic systems including bacterial, yeast, plant, and mammalian systems, using standard recombinant DNA techniques. These recombinant DNA techniques are described by Sambrook, J., Fritsch, E. F. and Maniatis, T. *Molecular Cloning: A Laboratory Manual,* Second Edition, Cold Spring Harbor Laboratory Press, Cold Spring Harbor (1989), and Clark et al., *Plant Molecular Biology, A Laboratory Manual,* Springer-Verlag, Berlin, Heideiberg, (1997), both of which are incorporated herein by reference.

For example, the silk proteins may be expressed in plants such as *Arabidopsis* or soy somatic embryos as described by Yang in patent application WO 01/90389, incorporated herein by reference. Additionally, silk analog proteins may be expressed in the endoplasmic reticulum of the leaves or tubers of transgenic tobacco and potato plants, as described in patent application DE 10113781, incorporated herein by reference. Silk proteins expressed in plants are soluble and can be redissolved in aqueous buffer after precipitation (Scheller et al., DE 10113781). Other suitable plant hosts include, but are not limited to, soybean, rapeseed (*Brassica napus, B. campestris*), pepper, sunflower (*Helianthus annus*), cofton (*Gossypium hirsutum*), corn, alfalfa (*Medicago sativa*), wheat (Triticum sp), barley (*Hordeum vulgare*), oats (*Avena sativa,* L), sorghum (*Sorghum bicolor*), rice (*Oryza sativa*), cruciferous vegetables (broccoli, cauliflower, cabbage, parsnips, etc.), melons, carrots, celery, parsley, tomatoes, strawberries, peanuts, grapes, grass seed crops, sugar beets, sugar cane, beans, peas, rye, flax, hardwood trees, softwood trees, and forage grasses.

Alternatively, the silk proteins may be expressed in mammalian cells such as bovine mammary epithelial alveolar cells or baby hamster kidney cells, as described by Lazaris et al. in *Science* 295:472–476 (2002), incorporated herein by reference. In both mammalian expression systems, the silk proteins were excreted into the culture media. Silk proteins expressed in mammalian cells are soluble and can be redissolved in aqueous buffer after precipitation (Lazaris et al. in *Science* 295:472–476 (2002)). In addition, the silk proteins may be expressed in transgenic animals, which secrete the proteins in their milk or urine, as described by Clark et al. in published U.S. patent application Ser. No. 2001/0042255 and Karatzas et al. in patent application WO 99/47661, both of which are incorporated herein by reference.

In the preferred embodiment of the present invention, the water-soluble silk proteins are expressed in microbial systems. Suitable microbial expression systems include, but are not limited to, *Escherichia, Bacillus, Saccharomyces, Schizosaccharomyces, Pichia, Aspergillus,* and *Streptomyces.* For example, the silk analog proteins DP-1A, DP-1B, and DP-2A may be expressed in *E. coli, Bacillus subtilis,* or *Pichia pastoris,* as described by Fahnestock (U.S. Pat. No. 6,268,169). In the most preferred embodiment, the spider silk analog protein DP-2A is expressed in *E. coli.* The spider silk protein, which is produced in a microbial host, is purified by the method described by Fahnestock et al. (copending, co-owned U.S. patent application Ser. No. 10/704,337, filed Nov. 7, 2003, entitled "A Method for Purifying and Recovering Silk Proteins in Soluble Form and Uses Thereof"), incorporated herein by reference, so that the recovered protein is water soluble. Specifically, the spider silk protein is precipitated from the cell extract by the addition of a salt, such as ammonium sulfate, at a temperature below about 20° C. and the recovered protein redissolves in water.

The water-soluble silk proteins may be used in skin care, hair care, and hair coloring compositions as film-forming agents in their native form or they may be modified to form derivatives, which provide a more beneficial effect. For example, the silk protein may be modified by conjugation to a polymer to reduce allergenicity as described by Olsen et al. in U.S. Pat. Nos. 5,981,718 and 5,856,451, both of which are incorporated herein by reference. Suitable modifying polymers include, but are not limited to, polyalkylene oxides, polyvinyl alcohol, poly-carboxylates, polyvinylpyrrolidone, and dextrans. In another example, the water-soluble silk proteins may be modified by selective digestion and splicing of other protein modifiers. For example, the water-soluble silk proteins may be cleaved into smaller peptide units by treatment with acid at an elevated temperature of about 60° C. The useful acids include, but are not limited to, dilute hydrochloric, sulfuric or phosphoric acids. Alternatively, digestion of the water-soluble silk proteins may be done by treatment with a base, such as sodium hydroxide, or enzymatic digestion using a suitable protease may be used. The peptides and proteins may be further modified to provide performance characteristics that are beneficial in specific applications for personal care products. The modification of proteins for use in personal care products is well known in the art. For example, commonly used methods are described by Olsen et al. in U.S. Pat. No. 6,303,752, Weisgerber et al. in U.S. Pat. No. 6,284,246, and by Dietz et al. in U.S. Pat. No. 6,358,501, all of which are incorporated herein by reference. Examples of modifications include, but are not limited to, ethoxylation to promote water-oil emulsion enhancement, siloxylation to provide lipophilic compatibility, and esterification to aid in compatibility with soap and detergent compositions. Additionally, the water-soluble silk proteins may be derivitized with functional groups including, but not limited to, amines, oxiranes, cyanates, carboxylic acid esters, silicone copolyols, siloxane esters, quaternized amine aliphatics, urethanes, polyacrylamides, dicarboxylic acid esters, and halogenated esters. The water-soluble silk proteins may also be derivitized by reaction with diimines and by the formation of metal salts.

In the compositions of the present invention, the expression "effective amount" of a water-soluble silk protein, or of an analog thereof corresponds to a proportion of from about 0.001 to about 90% by weight, but preferably from about 0.001 to about 60% by weight, most preferably from about 0.01 to about 20% by weight, relative to the total weight of the composition. This proportion may vary as a function of the type of skin care, hair care, or hair coloring composition.

The skin care, hair care, and hair coloring compositions of the present invention may also contain one or more conventional cosmetic or dermatological additives or adjuvants, including, but not limited to, fillers, surfactants, thixotropic agents, antioxidants, preserving agents, dyes, pigments, fragrances, thickeners, vitamins, hormones, moisturizers, UV absorbing sunscreens, wetting agents, cationic, anionic, nonionic or amphoteric polymers, and hair coloring active substances. These adjuvants are well known in the field of cosmetics and are described in many publications, for example see *Harry's Book of Cosmeticology,* 8th edition, Martin Rieger, ed., Chemical Publishing, New York (2000).

Among these adjuvants, the fillers are generally present in skin care, hair care, and hair coloring products in a maximum proportion of about 99.9% by weight relative to the total weight of the composition. These fillers, in the form of very fine powders, can be of natural or synthetic origin and include, but are not limited to, mineral powders, such as talc, kaolin, mica, silica, silicates, alumina, zeolites, hydroxyapatite, sericite, titanium dioxide, titanium micas, barium sulfate, calcium carbonate, calcium sulfate, bismuth oxychloride, boron nitride and metal powders such as aluminum powder; plant powder, such as corn starch, wheat starch or rice starch powders; organic powders, such as polyamide powder, polyester powder, polytetrafluoroethylene powder, the powder of fluorinated alkanes, polyethylene powder and other inert plastics. These various powders can also be coated, for example with metal salts of fatty acids, amino acids, lecithin, collagen, silicone compounds, fluoro compounds or with any common coating agent.

The skin care, hair care, and hair coloring compositions of this invention may also contain surfactants or wetting agents, preferably at about 0.05 to about 18%, more preferably at about 0.1 to about 15% by weight of the total composition. The terms "surfactants" and "wetting agents" as used herein refer to surface-active agents which, when added to water, cause it to penetrate more easily into, or spread on the surface of another material, by reducing the surface tension of the water at the water-air or water-oil interface. By "surface active agent" is meant any compound that reduces surface tension when dissolved in water or water solutions. The selection of a surfactant for this purpose presents a wide range of possibilities known in the art. Suitable surfactants include, but are not limited to, the following:

(1) anionic surfactants, such as metallic or alkanolamine salts of fatty acids for example sodium laurate and triethanolamine oleate; alkyl benzene sulfones, for example triethanolamine dodecyl benzene sulfonate; alkyl sulfates, for example sodium lauryl sulfate; alkyl ether sulfates, for example sodium lauryl ether sulfate (2 to 8 EO); sulfosuccinates, for example sodium dioctyl sulfonsuccinate; monoglyceride sulfates, for example sodium glyceryl monostearate monosulfate; isothionates, for example sodium isothionate; methyl taurides, for example Igepon T; acylsarcosinates, for example sodium myristyl sarcosinate; acyl peptides, for example Maypons and lamepons; acyl lactylates, polyalkoxylated ether glycollates, for example trideceth-7 carboxylic acid; phosphates, for example sodium dilauryl phosphate.

(2) cationic surfactants, such as amine salts, for example sapamin hydrochloride; quatenary ammonium salts, for example Quaternium 5, Quaternium 31 and Quaternium 18;

(3) amphoteric surfactants, such as imidazol compounds, for example Miranol; N-alkyl amino acids, such as sodium cocaminopropionate and asparagine derivatives; betaines, for example cocamidopropylebetaine (4) nonionic surfactants, such as fatty acid alkanolamides, for example oleic ethanolamide; esters or polyalcohols, for example Span; polyglycerol esters, for example that esterified with $C_1$ $2_{-1}$ 8 fatty acids and one or several OH groups; polyalkoxylated derivatives, for example polyoxy:polyoxyethylene stearate; ethers, for example polyoxyethe lauryl ether; ester ethers, for example Tween; amine oxides, for example coconut and dodecyl dimethyl amine oxides.

Mixtures of two or more of the above surfactants can be employed in the compositions according to the invention.

The skin care, hair care, and hair coloring compositions of this invention may also contain thixotropic or gelling agents, preferably at about 1 to about 20%, more preferably at about 3 to about 18% by weight of the total composition. Suitable thixotropic or gelling agents include, but are not limited to, stearates of aluminum, calcium, magnesium, potassium, sodium, or zinc; hydroxystearate, isostearate, laurate, linoleate, myristate, oleate, olivate, palmate, palmitate, tallowate, rosinate, and the like, and fatty acid esters of glycol, triglycerides, mixtures of fatty alcohols, cholesterol derivatives and in particular hydroxycholesterol, and clay minerals which swell in the presence of oil, and in particular those belonging to the montmorillonite group.

The skin care, hair care, and hair coloring compositions of this invention may also contain antioxidants, preferably at about 0.001 to about 10%, more preferably at about 0.01 to about 8% by weight of the total composition. Suitable antioxidants are ingredients which assist in preventing or retarding spoilage. Examples of antioxidants suitable for use in the compositions of the invention include, but are not limited to, potassium sulfite, sodium bisulfite, sodium erythrobate, sodium metabisulfite, sodium sulfite, propyl gallate, cysteine hydrochloride, butylated hydroxytoluene, butylated hydroxyanisole, and the like.

The skin care, hair care, and hair coloring compositions of this invention may also contain preserving agents, preferably at about 0.001 to about 8%, more preferably at about 0.01 to about 5% by weight of the total composition. Suitable preserving agents include, but are not limited to, benzoic acid, benzyl alcohol, benzylhemiformal, benzylparaben, 5-bromo-5-nitro-1,3-dioxane, 2-bromo-2-nitropropane-1,3-diol, butyl paraben, phenoxyethanol, methyl paraben, propyl paraben, diazolidinyl urea, calcium benzoate, calcium propionate, captan, chlorhexidine diacetate, chlorhexidine digluconate, chlorhexidine dihydrochloride, chloroacetarnide, chlorobutanol, p-chloro-m-cresol, chlorophene, chlorothymol, chloroxylenol, m-cresol, o-cresol, DEDM Hydantoin, DEDM Hydantoin dilaurate, dehydroacetic acid, diazolidinyl urea, dibromopropamidine diisethionate, DMDM Hydantoin, and all of those disclosed on pages 570 to 571 of the CTFA Cosmetic Ingredient Handbook, Second Edition, 1992, which is herein incorporated by reference.

The skin care, hair care, and hair coloring compositions of this invention may also contain dyes, preferably at about 0.1 to about 15%, by weight of the total composition. Suitable dyes include, but are not limited to, eosin derivatives such as D&C Red No. 21 and halogenated fluorescein derivatives such as D&C Red No. 27, D&C Red Orange No. 5 in combination with D&C Red No. 21 and D&C Orange No. 10.

The skin care, hair care, and hair coloring compositions of this invention may also contain pigments, preferably at about 0.1 to about 15% by weight of the total composition. Suitable pigments may be inorganic or organic or alternatively metal lakes and include, but are not limited to, titanium dioxide, zinc oxide, barium oxide, D&C Red No. 36 and D&C Orange No. 17, the calcium lakes of D&C Red Nos. 7, 11, 31 and 34, the barium lake of D&C Red No. 12, the strontium lake D&C Red No. 13, the aluminum lakes of FD&C Yellow No. 5, of FD&C Yellow No. 6, of D&C Red No. 27, of D&C Red No. 21, and of FD&C Blue No. 1, iron oxides, manganese violet, chromium oxide, ultramarine blue, and carbon black particles.

The skin care, hair care, and hair coloring compositions of this invention may also contain fragrances, preferably at about 0.01 to about 10%, by weight of the total composition. Numerous fragrances, both natural and synthetic, are well known in the art. For example, Secondini (*Handbook of Perfumes and Flavors,* Chemical Publishing Co., Inc., New York, 1990), incorporated herein by reference, describes many of the natural and synthetic fragrances used in cosmetics. Suitable natural fragrances include, but are not limited, to jasmines, narcissus, rose, violet, lavender, mint, spice, vanilla, anise, amber, orange, pine, lemon, wintergreen, rosemary, basil, and spruce. Suitable synthetic fragrances include, but are no limited to, acetaldehyde, C7 to C16 alcohols, benzyl acetate, butyric acid, citric acid, isobutyl phenyl acetate, linalyl butyrate, malic acid, menthol, phenyl ethyl cinnamate, phenyl propyl formate, tannic acid, terpineol, vanillin, amyl salicylate, benzaldehyde, diphenyl ketone, indole, and the like.

The skin care, hair care, and hair coloring compositions of this invention may also contain thickeners, preferably at about 0.001 to about 25%, more preferably at about 0.1 to about 15%, by weight of the total composition. Suitable thickeners include, but are not limited to, starch; gums, such as gum arabic or xanthan gum; carbomer polymers, such as Carbopol 941, 940, 934, and Ultrez 10; kaolin or other clays, ethylene glycol monostearate, carboxyvinyl polymer, acrylic copolymers, hydroxyethyl cellulose, and hydroxypropyl cellulose.

The skin care, hair care, and hair coloring compositions of this invention may also contain vitamins and/or coenzymes, preferably at about 0.001 to about 10%, preferably at about 0.01% to about 8%, most preferably at about 0.05% to about 5% by weight of the total composition. Suitable vitamins include, but are not limited to, ascorbic acid and derivatives thereof; the B vitamins, such as thiamine, riboflavin, pyridoxin, and the like; vitamin A and derivatives thereof; vitamin E and derivatives thereof; vitamin D and vitamin K; as well as coenzymes such as thiamine pyrophosphate, flavin adenine dinucleotide, folic acid, pyridoxal phosphate, tetrahydrofolic acid, and the like.

The skin care, hair care, and hair coloring compositions of this invention may also contain hormones, preferably at about 0.0001 to about 0.01% by weight of the total composition. Suitable hormones include, but are not limited to, estrogen, progesterone, pregnenolone, testosterone, estradiol, hydrocortisone, and cortisone.

The skin care, hair care, and hair coloring compositions of this invention may also contain moisturizers, preferably at about 0.1 to about 30%, preferably at about 0.5 to about 25%, most preferably at about 1 to about 20% by weight of the total composition. These moisturizers include water-soluble, low molecular weight moisturizers, fat-soluble, low molecular weight moisturizers, water-soluble, high molecular weight moisturizers and fat-soluble, high molecular weight moisturizers. Suitable water-soluble, low molecular weight moisturizers include, but are not limited to, serine, glutamine, sorbitol, mannitol, pyrrolidone-sodium carboxylate, glycerin, propylene glycol, 1,3-butylene glycol, ethylene glycol, polyethylene glycol (polymerization degree n=2 or more), polypropylene glycol (polymerization degree n=2 or more), polyglycerin (polymerization degree n=2 or more), lactic acid and lactate. Suitable fat-soluble, low molecular weight moisturizers include, but are not limited to, cholesterol and cholesterol ester. Suitable water-soluble, high molecular weight moisturizers include, but are not limited to, carboxyvinyl polymers, polyaspartate, tragacanth, xanthane gum, methyl cellulose, hydroxymethyl cellulose, hydroxyethyl cellulose, hydroxypropyl cellulose, carboxymethyl cellulose, water-soluble chitin, chitosan and dextrin. Suitable fat-soluble, high molecular weight moisturizers include, but are not limited to, polyvinylpyrrolidone-eicosene copolymers, polyvinylpyrrolidone-hexadecene copolymers, nitrocellulose, dextrin fatty acid ester and high molecular silicone.

The skin care, hair care, and hair coloring compositions of this invention may also contain UV absorbing sunscreens, preferably at about 0.001 to about 20%, more preferably at about 0.01 to about 10%, most preferably at about 0.05 to about 8% by weight of the total composition. UV absorbing sunscreens are herein defined as substances that absorb ultraviolet light of wavelengths between 290 to 329 nm. Suitable sunscreens include, but are not limited to, para-aminobenzoic acid, ethyl para-aminobenzoate, amyl para-aminobenzoate, octyl para-aminobenzoate, ethylene glycol salicylate, phenyl salicylate, octyl salicylate, benzyl salicylate, butylphenyl salicylate, homomenthyl salicylate, benzyl cinnamate, 2-ethoxyethyl para-methoxycinnamate, octyl para-methoxycinnamate, glyceryl mono(2-ethylhexanoate) dipara-methoxycinnamate, isopropyl para-methoxycinnamate, diisopropyl-diisopropylcinnamic acid ester mixtures, urocanic acid, ethyl urocanate, hydroxymethoxybenzophenone, hydroxymethoxybenzophenonesulfonic acid and salts thereof, dihydroxymethoxybenzophenone, sodium dihydroxymethoxybenzophenonedisulfonate, dihydroxybenzophenone, tetrahydroxybenzophenone, 4-tert-butyl-4'-methoxydibenzoylmethane, 2,4,6-trianilino-p-(carbo-2'-ethylhexyl-1'-oxy)-1,3,5-triazine, and 2-(2-hydroxy-5-methylphenyl)benzotriazole.

The skin care, hair care, and hair coloring compositions of this invention may also contain film-forming polymers, preferably at about 0.01 to about 20%, more preferably at about 0.01% to about 10%, by weight of the total composition. These polymers serve as conditioners to coat the skin or hair, or to coat particles that are present in the composition. These polymers may be cationic, anionic, nonionic, or amphoteric. Cationic polymers are herein defined as synthetic or natural polymers that contain, or have been modified to contain, positively charged groups and/or groups that can ionize to positively charged groups. Suitable cationic polymers, include, but are not limited to, cationized cellulose, cationized guar gum, diallyly quaternary ammonium salt/acrylamide copolymers, quaternized polyvinylpyrrolidone and derivatives thereof, polyquaternium-1, polyquaternium-2, polyquaternium-5, polyquaternium-6, polyquaternium-7, polyquaternium-8, polyquaternium-9, polyquaternium-11, polyquaternium-12, polyquaternium-13, polyquaternium-14, polyquaternium-15, polyquaternium-16, polyquaternium-17, polyquaternium-18, polyquaternium-19, polyquaternium-20, polyquaternium-22, polyquaternium-27, polyquaternium-28, polyquaternium-29, polyquaternium-30, and mixtures thereof, wherein the compound designation is the name adopted for the compound by the Cosmetic, Toiletry and Fragrance Association, and found in the CTFA International Cosmetic ingredient Dictionary, J. Nikitakis, ed., Cosmetic, Toiletry and Fragrance Association, Inc., Washington, D.C. (1991).

Anionic polymers are herein defined as synthetic or natural polymers that contain, or have been modified to contain, negatively charged groups and/or groups that can ionize to negatively charged groups. Suitable anionic polymers, include, but are not limited to, polyacrylic acid, polymethacrylic acid, carboxymethylcellulose, hydroxymethylcellulose, and starch.

Nonionic polymers are herein defined as synthetic or natural polymers that do not contain any charged groups. Suitable nonionic polymers, include, but are not limited to, polyvinylpyrrolidone, polyvinyl alcohol, polyethylene glycol, polyvinylacetate, polysiloxanes, and copolymers of vinylpyrrolidone and vinyl acetate.

Amphoteric polymers are herein defined as synthetic or natural polymers that contain both negatively and positively charged groups and/or groups that can ionize to give positively and negatively charged groups. Suitable amphoteric polymers are described by Marchi et al. In U.S. Pat. No. 5,643,672, incorporated herein by reference. Examples include, but are not limited to, polymers resulting from the copolymerization of a monomer derived from a vinyl compound carrying a carboxyl group, such as acrylic acid, methacrylic acid, maleic acid and alpha-chloroacrylic acid, and a basic monomer derived from a substituted vinyl compound containing at least one basic nitrogen atom, such as dialkylaminoalkyl methacrylates and acrylates and dialkylaminoalkylmethacrylamides and -acrylamides, products sold by the company National Starch under the name Amphomer, methyl methacrylate/ethyldimethylcarboxymethylammonium methacrylate copolymers, such as the products sold by Chimex under the name Mexomer PX (CTFA name: "polyquaternium-30"), methacryloylethylbetaine/methacrylate copolymer sold by Sandoz under the name Diaformer, the methacryloylethylbetaine/methacrylate copolymer sold by Amerchol under the name Amersette, polysiloxane polyorganobetaine copolymers sold by Goldschmidt under the name Abil B 9950 (CTFA Name: "Dimethicone PropylPG-Betaine"), the polydimethylsiloxane containing alkylphosphobetaine groups sold by Siltech under the name Pecosil SPB-1240, and the oxyethyleneoxypropylene organobetaine/siloxane copolymer sold by Goldschmidt under the name BC 1610.

The compositions of the present invention may also include an effective amount of one or more other natural or recombinant proteins that enhance the film-forming and coating properties of the water-soluble silk proteins or provide other desirable properties. An effective amount of these additional proteins is herein defined as a proportion from about 0.001 to about 60% by weight, more preferably from about 0.01 to about 20% by weight relative to the total weight of the composition. This proportion may vary as a function of the type of skin care, hair care, or hair coloring composition. Every protein molecule may be considered to be a polymer of amino acids. There are 20 naturally occurring amino acids, each with a common backbone combined with one of 20 variable side chains. Amino acids are commonly classified as either neutral, anionic, or cationic amino acids based on the charge of the variable side chain. The naturally occurring anionic amino acids include aspartic acid and glutamic acid, both of which have a carboxylate group at the termini of their respective variable side chains. The naturally occurring cationic amino acids include lysine, arginine and histidine, all of which comprise an amino group in their respective variable side chains. Amino acids may also be modified to result in a net cationic charge. All such amino acids are considered herein to be "cationic amino acids".

The most advantageous proteins to use in the composition will depend on the specific composition. For example, skin care and hair care products are generally in the pH range of 2.0 to 10.0. Proteins having a predominance of anionic amino acids, relative to cationic amino acids, are likely to be negatively charged at the general pH range of these products. Conversely, proteins having a relative abundance of cationic amino acids are likely to be positively charged under similar conditions. It is preferred that the amino acid composition of the additional natural or recombinant proteins of the present invention contain a preponderance of anionic amino acids relative to cationic amino acids, so that the proteins are negatively charged at the general pH range of skin care and hair care products. Specifically, the compositions of the present invention preferably comprise an additional natural or recombinant protein, wherein the molar ratio of anionic amino acids to cationic amino acids is at least 1.1:1, preferably from about 1.1:1 to 25:1, and more preferably from about 1.1:1 to 15:1. The term "molar ratio of anionic amino acids to cationic amino acids" of the natural or recombinant protein in the present invention is herein defined as the total molar amount of anionic amino acids (for example, adding the individual molar amount of the anionic amino acids, such as aspartic acid and glutamic acid) in relation to the total molar amount of cationic amino acids (for example, adding the individual molar amount of lysine, arginine and histidine) in the protein. The molar ratio of anionic amino acids to cationic amino acids may be readily calculated based on the overall amino acid composition of the natural or recombinant protein or mixtures of natural or recombinant proteins. Such compositions are frequently known in the art. Alternatively, the amino acid composition of any protein may be determined using techniques known to those skilled in the art, which include, but are not limited to automated amino acid analysis and high pressure liquid chromatography. Such techniques separate the individual amino acids, and the molar ratio of anionic to cationic amino acids may be determined.

Furthermore, the additional natural or recombinant proteins for use in the compositions of the present invention may comprise sulfur-containing amino acids to provide a protective effect against ultraviolet light or chemical damage to the skin and hair. The preferred natural or recombinant proteins of this invention are characterized in that they contain at least about 0.25%, preferably from about 0.25 to about 15%, and more preferably from about 0.25 to about 5.0% by weight of a sulfur containing amino acid. The term "sulfur-containing amino acids" is herein defined as any amino acid, natural or synthetic, containing sulfur in any form, including, but not limited to, sulfhydryl groups or disulfide bonds. Sulfur-containing amino acids suitable for the present invention include, but are not limited to, cysteine, cystine, methionine, and their respective derivatives and synthetic analogues.

The preferred natural or recombinant proteins for use in this invention include, but are not limited to, wheat, oat, almond, and soy proteins, collagen, keratins, gelatin, elastin, fibronectin, and soluble reticulin. The natural or recombinant proteins may be used in their native form or they may be modified to alter their ionic charge, for example by sulfonation or succinylation, as described above. These proteins may also be in the form of a digest by cleaving them into smaller peptide units, as described above.

According to one embodiment of the present invention, the compositions are anhydrous and comprise a fatty phase in a proportion generally of from about 10 to about 90% by weight relative to the total weight of the composition, wherein the fatty phase contains at least one liquid, solid or semi-solid fatty substance. The fatty substances include, but are not limited to oils, fats, waxes, gums, and so-called pasty fatty substances. The oils in the fatty phase may be of mineral, animal, plant or synthetic origin, and may or may not be volatile at room temperature.

Oils of mineral origin include, but are not limited to, liquid paraffin and liquid petroleum jelly. Oils of animal origin include, but are not limited to, squalene and squalane. Oils of plant origin include, but are not limited to, sweet almond oil, beauty-leaf oil, palm oil, avocado oil, jojoba oil, sesame oil, olive oil, castor oil and cereal germ oils such as, for example, wheatgerm oil. Synthetic oils include, but are not limited to:

(1) esters of the following formula:

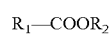

in which:
R$_1$ represents a higher fatty acid residue containing from 7 to 20 carbon atoms, and
R$_2$ represents a hydrocarbon-based radical containing from 3 to 30 carbon atoms.

These esters, include, but are not limited to: purcellin oil, butyl myristate, isopropyl myristate, cetyl myristate, isopropyl palmitate, butyl stearate, hexadecyl stearate, isopropyl stearate, octyl stearate, isocetyl stearate, decyl oleate, hexyl laurate, isononyl isononanoate and esters derived from lanolic acid, such as isopropyl lanolate and isocetyl lanolate. Other synthetic oils include, but are not limited to, isododecane, isohexadecane, polyisobutenes and hydrogenated polyisobutene, as well as acetylglycerides, octanoates and decanoates of polyalcohols such as those of glycol and of glycerol, ricinoleates of alcohols or of polyalcohols, such as cetyl ricinoleate, propylene glycol dicaprylate and diisopropyl adipate;

(2) fatty alcohols including, but not limited to, oleyl alcohol, linoleyl alcohol, linolenyl alcohol, isostearyl alcohol and octyldodecanol;

(3) ethoxylated oils and fats, including but not limited to, triglycerides with a polyethylene glycol chain inserted, ethoxylated mono and d i-glycerides, polyethoxylated la nolins, ethoxylated butter derivatives, polyethylene glycol derivatives of glyceryl cocoate, glyceryl caproate, glyceryl caprylate, glyceryl tallowate, glyceryl palmate, glyceryl stearate, glyceryl laurate, glyceryl oleate, glyceryl ricinoleate, and glyceryl fatty esters derived from triglycerides, such as palm oil, almond oil, and corn oil, glyceryl tallowate, glyceryl cocoate, and polyethylene glycol based polyethoxylated fatty alcohols such as PEG 40 hydrogenated castor oil (commercially available under the tradename Cremophor (RTM) from BASF), PEG 7 glyceryl cocoate and PEG 20 glyceryl laurate (commercially available from Henkel under the tradenames Cetiol (RTM) HE and Lamacit (RTM) GML 20 respectively), and polyethylene glycol ethers of ceteryl alcohol such as Ceteareth 25 (available from BASF under the trade name Cremaphor A25).

(4) silicone oils including, but not limited to, optionally functionalized linear polydiorganosiloxanes, cyclic polydiorganosiloxanes and in particular cyclotetra- and -pentadimethicones and organopolysiloxanes such as alkyl, alkoxy or phenyl dimethicones, and in particular phenyltrimethicone;

(5) fluoro oils including, but not limited to, fluoroalkanes and fluoropolyethers, partially fluorinated hydrocarbon-based oils, and fluoropolymers represented by the monomer unit:

$CH_2-CH_x-F_y$ wherein $X=1$ or 2, and $y=1$, 2, or 3.

The waxes in the fatty phase may be of mineral, fossil, animal, plant or synthetic origin or alternatively can be hydrogenated oils or fatty esters which are solid at 25° C. The mineral waxes, include, but are not limited to, microcrystalline waxes, paraffin, petroleum jelly and ceresine.

The fossil waxes, include, but are not limited to, ozocerite and montan wax. The waxes of animal origin, include, but are not limited to, beeswax, spermaceti, lanolin wax and derivatives obtained from lanolin such as lanolin alcohols, hydrogenated lanolin, hydroxylated lanolin, acetylated lanolin, lanolin fatty acids and acetylated lanolin alcohol. The waxes of plant origin, include, but are not limited to, candelilla wax, carnauba wax, Japan wax and cocoa butter. The synthetic waxes, include, but are not limited to, ethylene homopolymers, seracite, shea butter, and copolymers of ethylene and of a monomer corresponding to the formula:

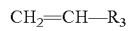

$CH_2=CH-R_3$ in which: $R_3$ represents an alkyl radical containing from 1 to 30 carbon atoms or an aryl or aralkyl radical. The alkyl radical of 1 to 30 carbon atoms is preferably a methyl, ethyl, propyl, isopropyl, butyl, decyl, dodecyl or octadecyl radical. Waxes obtained by Fisher-Tropsch synthesis and silicone waxes may also be used.

The hydrogenated oils which are solid at 25° C. include, but are not limited to, hydrogenated castor oil, hydrogenated palm oil, hydrogenated tallow and hydrogenated coconut oil. The fatty esters which are solid at 25° C. include, but are not limited to, propylene glycol monomyristate and myristyl myristate. Waxes which can be used in the compositions according to the invention include, but are not limited to, cetyl alcohol, stearyl alcohol, mono-, di- and triglycerides which are solid at 25° C., stearic monoethanolamide, colophony and its derivatives such as glycol abietate and glyceryl abietate, sucroglycerides and calcium, magnesium, zinc and aluminum oleates, myristates, lanolates, stearates and dihydroxystearates.

The pasty-type fatty substances can be of mineral, animal, plant or synthetic origin. The pasty fatty substances include, but are not limited to, synthetic esters such as arachidyl propionate, polyvinyl laurate, polyethylene waxes and organopolysiloxanes such as alkyldimethicones, alkoxydimethicones or dimethicone esters.

These anhydrous compositions can be in various forms including, but not limited to, an oily gel, solid products, such as compacted or cast powders, or alternatively sticks such as, for example lipsticks. When the compositions according to the present invention are in the form of an oily gel, they generally contain a thixotropic or gelling agent, examples of which are given above. The thixotropic agents can be present in various proportions depending on the desired texture of the compositions. However, in most cases, they are present in a proportion of from about 1 to about 20% by weight relative to the total weight of the composition.

The anhydrous compositions of the present invention may be used in particular as skin care, skin cleansing, or make-up products. When they are present in the form of make-up products, they can be foundations, mascaras, eyeliners, lipsticks, eyeshadows or blushers. These compositions are generally colored and contain dyes and/or pigments as cosmetic adjuvants, which are described above.

According to another embodiment of the present invention, the compositions are stable dispersions in the form of a water-in-oil (W/O) or oil-in-water (O/W) emulsion, which comprise: a fatty phase, as described above, in a proportion of from about 0.1 to about 50% by weight relative to the total weight of the emulsion, the said fatty phase containing at least one water-soluble silk protein or derivative thereof, in a proportion of from about 0.001 to about 60% by weight relative to the total weight of the emulsion; an aqueous phase in a proportion of from about 50 to about 98.9% by weight relative to the total weight of the emulsion; and at least one emulsifier in a proportion of from about 1 to about 10% by weight relative to the total weight of the emulsion. Suitable emulsifiers are well known in the field of cosmetic products. For example, water-in-oil emulsifiers include, but are not limited to, sterols such as cholesterol and its associated esters and alcohols, lanolin, calcium oleate and other fatty acid soaps of divalent metals, beeswax, and polyhydric alcoholics of fatty acids such as glyceryl monostearate and sorbitan sesquioleate. Suitable oil-in-water emulsifiers include, but are not limited to, ordinary soaps, partially sulfated fatty alcohols, Cetomacrogol B.P., polyethoxylated esters known as Spans, cetydimethylbenzyl ammonium chloride, and gums and gum substitutes.

These emulsions, which are in the form of creams, have good film-forming properties and give a very satisfactory sensation after they have been applied. Such emulsions can be used as skin care, skin cleansing, or make-up products. When these compositions are skin care products, they can be anti-wrinkle products for improving the appearance of the skin. When these compositions are make-up products, they may be foundations or mascaras, containing a certain proportion of the pigments and/or dyes described above.

In another embodiment of the present invention, the compositions are hair care compositions. Hair care compositions are herein defined as compositions for the treatment of hair, including but not limited to shampoos, conditioners, hair treatment creams, aerosols, gels, hair sprays, set lotions, blow styling lotions, hair relaxing compositions, permanent wave first agents, permanent wave second agents, and mousses. The hair care compositions of the present invention comprise an effective amount of water-soluble silk protein or derivative thereof in a cosmetically acceptable medium. An effective amount of a water-soluble silk protein or derivative thereof for use in a hair care composition is herein defined as a proportion of from about 0.001 to about 90% by weight relative to the total weight of the composition. Components of a cosmetically acceptable medium for hair care compositions are described by Omura et al. in U.S. Pat. No. 6,139,851 and Cannell et al. in U.S. Pat. No. 6,013,250, both of which are incorporated herein by reference. For example, these hair care compositions can be aqueous, alcoholic or aqueous-alcoholic solutions, the alcohol preferably being a monohydric alcohol such as ethanol or isopropanol, in a proportion of from about 1 to about 75% by weight relative to the total weight for the aqueous-alcoholic solutions. The hair care compositions may also contain polyhydric alcohols including, but not limited to, ethylene glycol, propylene glycol, 1,3 butylene glycol, glycerine, sorbitol, and polyethylene glycol. Additionally, the hare care compositions may contain one or more conventional cosmetic or dermatological additives or adjuvants, as described above.

In another embodiment of the present invention, the compositions are hair coloring compositions. Hair coloring compositions are herein defined as compositions for the coloring, dyeing, or bleaching of hair. The hair coloring compositions of the present invention comprise an effective amount of water-soluble silk protein or derivative thereof in a cosmetically acceptable medium. An effective amount of a water-soluble silk protein or derivative thereof for use in a hair coloring composition is herein defined as a proportion of from about 0.001 to about 60% by weight relative to the total weight of the composition. These hair coloring compositions contain hair coloring active substances, which include, but are not limited to, oxidative dyes, direct dyes, or a mixture thereof, and peroxygen-based oxidizing agents for the bleaching of hair.

Oxidative dyes, which provide hair color that lasts for about 4 to 6 weeks, contain a mixture of a peroxygen-based oxidizing agent and an oxidizable coloring agent. Suitable peroxygen-based oxidizing agents include, but are not limited to, inorganic peroxygen oxidizing agents such as hydrogen peroxide, preformed organic peroxyacid oxidizing agents, organic peroxide oxidizing agents, and mixtures thereof. The oxidative hair coloring agents are formed by oxidative coupling of primary intermediates, including but not limited to p-phenylenediamines, p-aminophenols, p-diaminopyridines, hydroxyindoles, aminoindoles, aminothymidines, or cyanophenols, with secondary intermediates, including, but not limited to phenols, resorcinols, m-aminophenols, m-phenylenediamines, naphthols, pyrazolones, hydroxyindoles, catechols or pyrazoles. The concentration of each oxidizing hair coloring agent is preferably at about 0.001 to about 3%, more preferably at about 0.01 to about 2% by weight of the total composition. The total combined level of oxidative hair coloring agents in the hair coloring compositions of this invention is preferably from about 0.001 to about 5%, more preferably from about 0.01 to about 4% by weight of the total composition.

Direct hair coloring active substances are preformed dyes, which do not require an oxidative effect in order to develop their color and are washed out of the hair more readily than the oxidative dyes. Suitable direct dyes include, but are not limited to, 4-hydroxypropylamino-3-nitrophenol, 4-amino-3-nitrophenol, 2-amino-6-chloro-4-nitrophenol, HC Blue 2, HC Yellow 4, HC Red 3, Disperse Violet 4, Disperse Black 9, HC Blue 7, HC Blue 12, HC Yellow 2, HC Yellow 12, Disperse Blue 3, Disperse Violet 1 and mixtures thereof.

Other components of a cosmetically acceptable medium for hair coloring compositions are described by Dias et al., in U.S. Pat. No. 6,398,821 and by Deutz et al., in U.S. Pat. No. 6,129,770, both of which are incorporated herein by reference. For example, hair coloring compositions may contain oxidizing acids, sequestrants, stabilizers, thickeners, buffers, carriers, surfactants, solvents, antioxidants, polymers, and conditioners, as described above.

The hair coloring compositions of the present invention may be prepared from an aqueous alkaline solution comprising an effective amount of a water-soluble silk protein, as described above, in a cosmetically acceptable medium for hair coloring compositions, and a basic substance to raise the pH to between about 8.0 to about 12.0. These basic substances include, but are not limited to, ammonium hydroxide, sodium hydroxide, and potassium hydroxide. This aqueous alkaline composition may be used to prepare oxidative hair coloring, direct hair coloring, and bleaching compositions by combining it with a suitable oxidative or direct dye or a peroxygen-based oxidizing agent, as described above.

The present invention also comprises a method for forming a protective film of water-soluble silk protein on skin or hair by applying one of the compositions described above comprising an effective amount of water-soluble silk protein to the skin or hair and allowing the formation of the protective film. The compositions of the present invention may be applied to the skin or hair by various means, including, but not limited to, spraying, brushing, and applying by hand. The water-soluble silk protein-containing composition is left in contact with the skin or hair for a period of time sufficient to form the protective film, preferably for at least about 0.1 to 60 min.

The present invention also comprises a method for coloring hair comprising applying a hair coloring composition comprising an effective amount of a water-soluble silk protein and at least one hair coloring active substance to the hair by means described above. This hair coloring composition is allowed to contact the hair for a period of time sufficient to cause coloration of the hair, preferably between about 5 to about 50 min. The hair coloring composition is then rinsed from the hair.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

The meaning of abbreviations used is as follows "wt %" means percent by weight, "qs" means as much as suffices, "EDTA" means ethylenediamine tetraacetate, "CFTA" means the Cosmetic, Toiletry and Fragrance Association, "POE" means polyoxyethylene, "PEG" means polyethylene glycol, "cSt" means centistokes.

The water-soluble silk protein referred to in the Examples is prepared by the method described by Fahnestock et al. in U.S. patent application Ser. No. 10/704,337, which is incorporated herein by reference.

Example 1

Hair Coloring Composition

A composition for oxidative dyeing of hair is made by mixing the following ingredients:

| | wt % |
| --- | --- |
| Ammonium lauryl sulfate (anionic surfactant) | 2.00 |
| Propylene glycol (moisturizer) | 4.00 |
| Ethoxydiglycol (solvent) | 2.00 |
| Monoethanolamine (pH adjuster) | 5.00 |
| Seaweed extract (conditioner) | 0.80 |
| Tetrasodium EDTA (chelating agent) | 0.80 |
| Isoascorbic acid (antioxidant) | 0.20 |
| Sodium sulfite (reducing agent) | 0.50 |
| Primary intermediates and couplers (dye) | 5.00 |
| Oleic acid (soap) | 12.50 |
| Cetearyl alcohol (opacifier) | 4.00 |
| Emulsifying wax (emulsifier) | 2.00 |
| Oleth-20 (nonionic surfactant) | 1.00 |
| Steareth-21 (nonionic surfactant) | 0.70 |
| Meadowfoam seed oil (oil) | 0.75 |
| Oleyl alcohol (oil) | 0.40 |
| Polyquaternium 10 (cationic surfactant) | 0.20 |
| Polyquaternium 28 (cationic surfactant) | 0.50 |
| Mica/titanium dioxide (pigment) | 0.30 |
| Water-soluble silk protein | 1.00 |
| Cibafast W liquid[1] (UV absorber) | 1.00 |
| Fragrance | 0.75 |
| Ammonium hydroxide (pH adjuster) | 5.00 |
| Wheat amino acids (conditioner) | 1.00 |
| Water | qs to 100 |

[1] Cibafast W Liquid is sodium isobutyl benzotriazole sulfonate, obtained from Ciba Specialty Chemicals, Basil, Switzerland.

The composition is made by first dissolving the first eight ingredients in water. The primary intermediates and couplers are then added with heat to dissolve. The remaining ingredients, except for the ammonium hydroxide, wheat amino acids, and fragrance, are mixed separately and added after the primary intermediates and couplers. The remaining water, ammonium hydroxide, wheat amino acids, and fragrance are finally added to the mixture.

Example 2

Aqueous Alkaline Composition

An aqueous alkaline composition suitable for mixing with a peroxide composition to form a hair bleach is prepared by mixing the following ingredients:

| | wt % |
| --- | --- |
| Erythrobic acid | 0.20 |
| Sodium sulfite | 0.50 |
| Propylene glycol | 4.00 |
| Ethoxydiglycol | 2.00 |
| Tetrasodium EDTA (38% aqueous Solution) | 0.80 |
| Ethanolamine | 5.00 |
| Hypnea musciformis extract/gellidiela acerosa/ extract, sargassum filipendula extract/sorbitol | 0.80 |
| Sodium benzotriazole sulfonate/buteth-3/propane tricarboxylic acid | 1.00 |
| Ammonium lauryl sulfate (28% aqueous solution) | 2.00 |
| Oleic acid | 12.50 |
| Cetearyl alcohol | 4.00 |
| Emulsifying wax | 2.00 |
| Oleth-20 | 1.00 |
| Steareth-21 | 0.70 |
| Meadowfoam seed oil | 0.75 |
| Oleyl alcohol | 0.40 |
| Polyquaternium-10 | 0.20 |
| Polyquaternium-28 | 0.50 |
| Mica/titanium dioxide (67:33) | 0.30 |
| Water-soluble silk protein | 1.00 |
| Silk protein peptides | 1.00 |
| Fragrance | 0.75 |
| Ammonium hydroxide (27.5% aqueous solution) | 5.00 |
| Water | qs to 100 |

This composition is useful for creating several hair coloring formulations, including oxidative hair coloring, direct deposit hair coloring, bleaching cremes and permanent waving compositions.

Example 3

Hair Bleach Composition

An emulsion is formed by mixing equal volumes of the aqueous alkaline composition of Example 2 and an aqueous hydrogen peroxide solution (6 wt %). This mixture is applied to natural light brown hair. The composition is left on the hair for five minutes, and then rinsed out with water. The resulting hair is lightened several shades.

Example 4

Hair Shampoo

A hair shampoo is prepared by mixing the following ingredients:

| CFTA Names | wt % |
| --- | --- |
| Self emulsifying glyceryl ester | 6.0 |
| Cetrimonium chloride | 3.5 |
| Dicetyldimonium chloride | 3.0 |
| Water-soluble silk protein | 0.1 |
| Cetearyl alcohol | 2.0 |
| Trimetylsyllamodimethicone | 0.7 |
| Ammonium lauryl sulfate | 25 |
| Cocamidopropyl betaine | 10 |
| Sodium lauryl sarcosinate | 5.0 |
| Water | qs to 100 |

Example 5

Hair Conditioner

A hair conditioner is prepared by mixing the following ingredients:

| CFTA Names | wt % |
| --- | --- |
| Self emulsifying glyceryl ester | 6.0 |
| Cetrimonium chloride | 3.5 |
| Dicetyldimonium chloride | 3.0 |
| Water-soluble silk protein | 0.1 |
| Cetearyl alcohol | 2.0 |
| Trimetylsyllamodimethicone | 0.7 |
| Menthol | 0.1 |
| Phytolipid and hyaluronic Acid | 0.1 |
| Apricot seed (Apricot Kernel Powder produced by Alban Muellen, Inc. of Paris, France) | 0.25 |
| Pearlizing agent | 0.8 |
| Methyl gluceth-20 | 0.25 |
| Polyquaternium-4 | 0.1 |
| Water | qs to 100 |

Example 6

Emulsions for Skin Care

Three variations of skin emulsion compositions are prepared by mixing the following ingredients:

| | Comp. #1 wt % | Comp. #2 wt % | Comp. #3 wt % |
| --- | --- | --- | --- |
| Mineral Oil | 4 | 4 | 4 |
| Petroselinic acid (triglyceride) ex Elysion | 1.15 | 2 | 3 |
| Green Tea Polyphenols | 0 | 2 | 0 |
| Water-soluble silk protein | 0.001 | 0.01 | 1 |
| Quercetin | 0.5 | 0 | 0 |
| Brij 56[1] | 4 | 4 | 4 |
| Alfol 16RD[2] | 4 | 4 | 4 |
| Triethanolamine | 0.75 | 0.75 | 0.75 |
| Butane-1,3-diol | 3 | 3 | 3 |
| Xanthan gum | 0.3 | 0.3 | 0.3 |
| Perfume | qs | qs | qs |
| Butylated hydroxy toluene | 0.01 | 0.01 | 0.01 |
| Water | qs to 100 | qs to 100 | qs to 100 |

[1] Brij 56 is cetyl alcohol POE (10)
[2] Alfol 16RD is cetyl alcohol

Example 7

Thicker Emulsions

Three variations of thicker emulsion compositions are prepared by mixing the following ingredients:

| Full Chemical or Trade Name | Comp. #1. wt % | Comp. #2. wt % | Comp. #3 wt % |
| --- | --- | --- | --- |
| Coriander seed oil ex Loders Croklaan (PA triglyceride 60–75% of total fatty acids) | 2 | 3 | 1.5 |
| Water-soluble silk protein | 1 | 2 | 1.5 |
| Disodium EDTA (Sequesterene Na$_2$) | 0.05 | 0.05 | 0.05 |
| Magnesium aluminum silicate Veegum Ultra | 0.6 | 0.6 | 0.6 |
| Methyl paraben | 0.15 | 0.15 | 0.15 |
| Simethicone | 0.01 | 0.01 | 0.01 |
| Butylene glycol 1,3 | 3.0 | 3.0 | 3.0 |
| Hydroxyethylcellulose | 0.5 | 0.5 | 0.5 |
| Glycerine, USP | 2.0 | 2.0 | 2.0 |
| Xanthan gum | 0.2 | 0.2 | 0.2 |
| Triethanolamine | 1.2 | 1.2 | 1.2 |
| Stearic acid | 3.0 | 3.0 | 3.0 |
| Propyl paraben NF | 0.1 | 0.1 | 0.1 |
| Glyceryl hydrostearate | 1.5 | 1.5 | 1.5 |
| Stearyl alcohol | 1.5 | 1.5 | 1.5 |
| Isostearyl palmitate | 6.0 | 6.0 | 6.0 |
| C12–15 alcohols | 3.0 | 3.0 | 3.0 |
| Octanoate | 3.0 | 3.0 | 3.0 |
| Dimethicone (50 cSt) | 1.0 | 1.0 | 1.0 |
| Cholesterol NF | 0.5 | 0.5 | 0.5 |
| Sorbitan stearate | 1.0 | 1.0 | 1.0 |
| Butylated Hydroxytoluene | 0.05 | 0.05 | 0.05 |
| Tocopheryl acetate | 0.1 | 0.1 | 0.1 |
| PEG-100 stearate | 2.0 | 2.0 | 2.0 |
| Sodium stearoyl lactylate | 0.5 | 0.5 | 0.5 |
| Hydroxycaprylic acid | 0.1 | 0.1 | 0.1 |
| Alpha-bisabolol | 0.2 | 0.2 | 0.2 |
| Water | qs to 100 | qs to 100 | qs to 100 |

We claim:

1. A skin care, hair care, or hair coloring composition comprising:
   (a) an effective amount of a water-soluble silk protein; and optionally
   (b) at least one cosmetic adjuvant selected from the group consisting of fillers, surfactants, thixotropic agents, antioxidants, preserving agents, dyes, pigments, fragrances, thickeners, vitamins, hormones, moisturizers, UV absorbing sunscreens, wetting agents, cationic polymers, anionic polymers, nonionic polymers, amphoteric polymers, and hair coloring active substances,
   wherein the water-soluble silk protein is expressed in microbial expression systems, is purified by precipitation at a temperature below about 20° C. and redissolves in water.

2. The composition of claim 1 wherein the effective amount of the water-soluble silk protein is from about 0.001 to about 90% by weight of the total weight of the composition.

3. The composition of claim 1 wherein the water-soluble silk protein is selected from the group consisting of the dragline spider silk proteins Spidroin 1 and Spidroin 2, spider silk proteins originating from the minor ampullate gland of *Nephila clavipes*, and spider silk proteins originating from the flagelliform gland of *Nephila clavipes*, and variants thereof.

4. The composition of claim 1 wherein the water-soluble silk protein is a spider dragline silk protein.

5. The composition of claim 4 wherein the spider silk dragline protein is defined by the formula:

[AGQGGYGGLGXQGAGRGGLGGQGAGAnGG]z
SEQ ID NO:5 wherein X=S, G or N; n=0–7 and z=1–75, and wherein the value of z determines the number of repeats in the variant protein and wherein the formula encompasses variations selected from the group consisting of:
   (a) when n=0, the sequence encompassing AGRGGLG-GQGAGAnGG is deleted;
   (b) deletions other than the poly-alanine sequence, limited by the value of n will encompass integral multiples of three consecutive residues;
   (c) the deletion of GYG in any repeat is accompanied by deletion of GRG in the same repeat; and
   (d) where a first repeat where n=0 is deleted, the first repeat is preceded by a second repeat where n=6; and
   wherein the full-length protein is encoded by a gene or genes and wherein said gene or genes are not endogenous to the *Nephila clavipes* genome.

6. The composition of claim 4 wherein the spider silk dragline protein is defined by the formula:

[GPGGYGPGQQGPGGYGPGQQGPGGYG-PGQQGPSGPGSAn]z SEQ ID NO:9 wherein n=6–10 and z=1–75 and wherein, excluding the poly-alanine sequence, individual repeats differ from the consensus repeat sequence by deletions of integral multiples of five consecutive residues consisting of one or both of the pentapeptide sequences GPGGY or GPGQQ and wherein the full-length protein is encoded by a gene or genes and wherein the gene or genes are not endogenous to the *Nephila clavipes* genome.

7. The composition of claim 5 wherein the spider dragline protein has a repeating unit having the amino acid sequence as set forth in SEQ ID NO:1, SEQ ID NO:2, or SEQ ID:3.

8. The composition of claim 4 wherein the spider dragline protein has a repeating unit having the amino acid sequence as set forth in SEQ ID) NO:4.

9. The composition of claim 1 wherein the water-soluble silk protein is in a derivatized form.

10. The composition of claim 9 wherein the water-soluble silk protein has been derivatized with a functional group selected from the group consisting of amines, oxanes, cyanates, carboxylic acid esters, silicone copolyols, siloxane esters, quaternized amine aliphatics, urethanes, polyacrylamides, dicarboxylic acid esters, and halogenated esters.

11. The composition of claim 1 wherein the composition further comprises an effective amount of a natural or recombinant protein, or a digest thereof.

12. The composition of claim 11 wherein the natural or recombinant protein is selected from the group consisting of wheat proteins, oat proteins, rice proteins, almond proteins, soy proteins, collagen, keratins, gelatin, elastin, fibronectin, and soluble reticulin.

13. The composition of claim 1, which is an anhydrous composition and contains 10 to 90% by weight, relative to the total weight of the composition, of a fatty phase, wherein the fatty phase contains at least one liquid, solid, or semi-solid fatty substance.

14. The composition of claim 13, wherein the fatty substance is selected from the group consisting of isododecane, hydrogenated polyisobutene, squalane, isononyl isononanoate, cyclotetra- and -pentadimethicones, phenyltrimethicone, ethylene homopolymers, ethoxylated fats and oils, fluoroalkanes, microcrystalline waxes, ozocerite, beeswax, seracite, shea butter, candelilla wax, arachidyl propionate, fluoropolymers represented by the monomer:

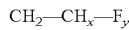

wherein x=1 or 2 , and y=1, 2 or 3, and copolymers of ethylene and of at least one monomer represented by the formula:

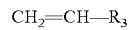

wherein $R_3$ is an alkyl radical containing from 1 to 30 carbon atoms or an aryl or aralkyl radical.

15. The composition of claim 1, which is in the form of an aqueous solution containing mono or polyhydric alcohols.

16. The composition of claim 1, which is in the form of a creme emulsion, a gel, a dry powder, an aerosol, a mousse, an alcohol-in-oil emulsion, an alcohol and water solution, an aqueous solution, or an emulsion solution.

17. The composition of claim 1 which is in the form of a powder and wherein the effective amount of the water-soluble silk protein is present along with a pigment or filler.

18. The composition of claim 1, which is in the form of an aqueous alkaline solution suitable for preparing compositions for coloring or bleaching hair.

19. The composition of claim 1, which is in the form of a stable dispersion of water-in-oil or oil-in-water type, and comprises:

(a) a fatty phase in a proportion of from about 0.1 to about 50% by weight relative to the total weight of the composition, wherein the fatty phase contains a water-soluble silk protein, or derivative thereof, in a proportion of from about 0.001 to about 90% by weight relative to the total weight of the composition;

(b) an aqueous phase in a proportion of from about 50 to about 98.9% by weight relative to the total weight of the composition; and (c) at least one emulsifier in a proportion of from about 1 to about 10% by weight relative to the total weight of the composition.

20. A method for forming a protective film of water-soluble silk protein on skin or hair comprising:

(a) applying to the skin or hair the composition of claim 1; and (b) allowing the formation of the water-soluble silk protein protective film on the skin or hair.

* * * * *

SEQUENCE LISTING

<160> NUMBER OF SEQ ID NOS: 4

<210> SEQ ID NO 1
<211> LENGTH: 101
<212> TYPE: PRT
<213> ORGANISM: artificial sequence

```
<220> FEATURE:
<223> OTHER INFORMATION: Monomer of spider silk DP-1A analog protein

<400> SEQUENCE: 1

Gly Ala Gly Arg Gly Gly Gln Gly Ala Gly Ala Ala Ala Ala Ala
1               5                   10                  15

Gly Gly Ala Gly Gln Gly Gly Tyr Gly Gly Leu Gly Ser Gln Gly Ala
            20                  25                  30

Gly Arg Gly Gly Leu Gly Gly Gln Gly Ala Gly Ala Ala Ala Ala
        35                  40                  45

Ala Ala Gly Gly Ala Gly Gln Gly Gly Leu Gly Ser Gln Gly Ala Gly
    50                  55                  60

Gln Gly Ala Gly Ala Ala Ala Ala Ala Gly Gly Ala Gly Gln Gly
65                  70                  75                  80

Gly Tyr Gly Gly Leu Gly Ser Gln Gly Ala Gly Gln Gly Gly Tyr Gly
                85                  90                  95

Gly Leu Gly Ser Gln
            100

<210> SEQ ID NO 2
<211> LENGTH: 101
<212> TYPE: PRT
<213> ORGANISM: artificial sequence
<220> FEATURE:
<223> OTHER INFORMATION: Monomer of spider silk DP-1B.9 analog protein

<400> SEQUENCE: 2

Gly Ala Gly Gln Gly Gly Tyr Gly Gly Leu Gly Ser Gln Gly Ala Gly
1               5                   10                  15

Arg Gly Gly Leu Gly Gly Gln Gly Ala Gly Ala Ala Ala Ala Ala
            20                  25                  30

Ala Gly Gly Ala Gly Gln Gly Gly Leu Gly Ser Gln Gly Ala Gly Gln
        35                  40                  45

Gly Ala Gly Ala Ala Ala Ala Ala Gly Gly Ala Gly Gln Gly Gly
    50                  55                  60

Tyr Gly Gly Leu Gly Ser Gln Gly Ala Gly Arg Gly Gly Gln Gly Ala
65                  70                  75                  80

Gly Ala Ala Ala Ala Ala Gly Gly Ala Gly Gln Gly Gly Tyr Gly
                85                  90                  95

Gly Leu Gly Ser Gln
            100

<210> SEQ ID NO 3
<211> LENGTH: 101
<212> TYPE: PRT
<213> ORGANISM: artificial sequence
<220> FEATURE:
<223> OTHER INFORMATION: Monomer of spider silk DP-1B.16 analog protein

<400> SEQUENCE: 3

Ser Gln Gly Ala Gly Gln Gly Gly Tyr Gly Gly Leu Gly Ser Gln Gly
1               5                   10                  15

Ala Gly Arg Gly Gly Leu Gly Gly Gln Gly Ala Gly Ala Ala Ala
            20                  25                  30

Ala Ala Ala Gly Gly Ala Gly Gln Gly Gly Leu Gly Ser Gln Gly Ala
        35                  40                  45

Gly Gln Gly Ala Gly Ala Ala Ala Ala Ala Gly Gly Ala Gly Gln
    50                  55                  60
```

-continued

```
Gly Gly Tyr Gly Gly Leu Gly Ser Gln Gly Ala Gly Arg Gly Gly Gln
65                  70                  75                  80

Gly Ala Gly Ala Ala Ala Ala Ala Gly Ala Gly Gln Gly Gly
                85                  90                  95

Tyr Gly Gly Leu Gly
            100

<210> SEQ ID NO 4
<211> LENGTH: 119
<212> TYPE: PRT
<213> ORGANISM: artificial sequence
<220> FEATURE:
<223> OTHER INFORMATION: Monomer of spider silk DP-2A analog protein

<400> SEQUENCE: 4

Gly Pro Ser Gly Pro Gly Ser Ala Ala Ala Ala Ala Ala Gly Pro Gly
1               5                   10                  15

Gln Gln Gly Pro Gly Gly Tyr Gly Pro Gly Gln Gln Gly Pro Gly Gly
                20                  25                  30

Tyr Gly Pro Gly Gln Gln Gly Pro Ser Gly Pro Gly Ser Ala Ala Ala
            35                  40                  45

Ala Ala Ala Ala Ala Gly Pro Gly Gly Tyr Gly Pro Gly Gln Gln Gly
        50                  55                  60

Pro Gly Tyr Gly Pro Gly Gln Gln Gly Pro Ser Gly Pro Gly Ser
65                  70                  75                  80

Ala Ala Ala Ala Ala Ala Ala Ala Gly Pro Gly Gly Tyr Gly Pro
                85                  90                  95

Gly Gln Gln Gly Pro Gly Gly Tyr Gly Pro Gly Gln Gln Gly Pro Gly
            100                 105                 110

Gly Tyr Gly Pro Gly Gln Gln
            115
```